(12) United States Patent
Desai et al.

(10) Patent No.: US 11,453,584 B2
(45) Date of Patent: Sep. 27, 2022

(54) HIGH THROUGHPUT METHANE PYROLYSIS REACTOR FOR LOW-COST HYDROGEN PRODUCTION

(71) Applicant: PALO ALTO RESEARCH CENTER INCORPORATED, Palo Alto, CA (US)

(72) Inventors: Divyaraj Desai, Hayward, CA (US); Todd Karin, Fairfield, CA (US); Jessica Louis Baker Rivest, Palo Alto, CA (US)

(73) Assignee: PALO ALTO RESEARCH CENTER INCORPORATED, Palo Alto, CA (US)

( * ) Notice: Subject to any disclaimer, the term of this patent is extended or adjusted under 35 U.S.C. 154(b) by 266 days.

(21) Appl. No.: 16/394,041

(22) Filed: Apr. 25, 2019

(65) Prior Publication Data

US 2020/0002165 A1    Jan. 2, 2020

Related U.S. Application Data

(60) Provisional application No. 62/692,558, filed on Jun. 29, 2018.

(51) Int. Cl.
*B01J 8/08*    (2006.01)
*C01B 3/26*    (2006.01)
(Continued)

(52) U.S. Cl.
CPC .......... *C01B 3/26* (2013.01); *B01J 8/125* (2013.01); *B01J 21/18* (2013.01); *B01J 35/12* (2013.01);
(Continued)

(58) Field of Classification Search
CPC ....................................................... B01J 8/125
See application file for complete search history.

(56) References Cited

U.S. PATENT DOCUMENTS

| | | |
|---|---|---|
| 1,107,926 A | 8/1914 | Frank |
| 1,418,385 A | 6/1922 | Masson |
| (Continued) | | |

FOREIGN PATENT DOCUMENTS

| | | |
|---|---|---|
| EP | 1462170 | 9/2004 |
| EP | 3446780 A1 | 2/2019 |
| (Continued) | | |

*Primary Examiner* — Stuart L Hendrickson
(74) *Attorney, Agent, or Firm* — Miller Nash LLP (57) ABSTRACT

A system for hydrocarbon decomposition comprising a reactor volume, a mechanism to distribute the liquid catalyst as a liquid mist, a distributor to distribute a hydrocarbon reactant, a heat source, a separator to separate the solid product from the liquid catalyst, a re-circulation path and mechanism to re-circulate the liquid catalyst, and an outlet for at least one gaseous product. A system to distribute a liquid to an enclosed volume as a mist has a plurality of orifices designed to break the liquid into a mist. A method to decompose a hydrocarbon reactant includes generating a mist of a liquid catalyst, heating the reactor volume, introducing a hydrocarbon reactant into the reactor volume to produce a solid product and a gaseous product, separating the solid product from the liquid catalyst, removing the solid and gaseous products from the reactor volume, and recirculating the liquid catalyst to the reactor volume.

9 Claims, 6 Drawing Sheets

(51) Int. Cl.
    *B01J 21/18*     (2006.01)
    *B01J 35/12*     (2006.01)
    *B01J 38/48*     (2006.01)
    *C07C 5/32*     (2006.01)
    *B01J 8/12*     (2006.01)

(52) U.S. Cl.
    CPC .............. *B01J 38/48* (2013.01); *C07C 5/321* (2013.01); *B01J 2203/06* (2013.01); *C01B 2203/1005* (2013.01); *C01B 2203/1041* (2013.01); *C01B 2203/1241* (2013.01)

(56) References Cited

U.S. PATENT DOCUMENTS

| | | |
|---|---|---|
| 1,756,877 A | 4/1930 | Paris, Jr. |
| 1,803,221 A | 4/1931 | Tyrer |
| 2,760,847 A | 8/1956 | Oblad et al. |
| 2,781,247 A | 2/1957 | Krejci |
| 2,782,101 A | 2/1957 | Heller |
| 2,882,216 A | 4/1959 | Viles |
| 3,156,734 A | 11/1964 | Happel |
| 3,490,869 A | 1/1970 | Heller |
| 3,625,026 A | 12/1971 | Cocker |
| 3,965,252 A | 6/1976 | Kmecak et al. |
| 4,888,052 A * | 12/1989 | Harris .................... C22B 26/12 75/588 |
| 4,983,278 A | 1/1991 | Cha et al. |
| 5,537,940 A | 7/1996 | Nagel et al. |
| 5,577,346 A * | 11/1996 | Malone .................... C01B 3/10 423/648.1 |
| 6,110,239 A | 8/2000 | Malone et al. |
| 6,350,289 B1 | 2/2002 | Holcombe et al. |
| 6,653,005 B1 | 11/2003 | Muradov |
| 6,663,681 B2 | 12/2003 | Kindig et al. |
| 6,670,058 B2 | 12/2003 | Muradov |
| 6,682,714 B2 | 1/2004 | Kingdig et al. |
| 6,685,754 B2 | 2/2004 | Kindig et al. |
| 6,719,047 B2 | 4/2004 | Fowler et al. |
| 7,588,746 B1 | 9/2009 | Muradov et al. |
| 8,034,321 B2 | 10/2011 | Mauthner et al. |
| 2003/0072705 A1 | 4/2003 | Kindig et al. |
| 2003/0130360 A1 | 7/2003 | Kindig et al. |
| 2009/0321966 A1 | 12/2009 | Sechrist |
| 2011/0088320 A1 | 4/2011 | Dietenberger et al. |
| 2015/0151274 A1* | 6/2015 | Lee .................... B01J 19/0006 422/187 |
| 2019/0055173 A1 | 2/2019 | Desai et al. |

FOREIGN PATENT DOCUMENTS

| | | |
|---|---|---|
| WO | 98/22385 | 5/1998 |
| WO | 03/045841 | 6/2003 |
| WO | 2019099795 A1 | 5/2019 |

\* cited by examiner

HIGH THROUGHPUT METHANE PYROLYSIS REACTOR FOR LOW-COST HYDROGEN PRODUCTION

RELATED APPLICATIONS

This application is a continuation of and claims priority to U.S. Provisional Patent Application No. 62/692,558, filed Jun. 29, 2018, which is incorporated herein by reference in its entirety.

TECHNICAL FIELD

This disclosure relates to hydrogen production, more particularly to methane pyrolysis for hydrogen production.

BACKGROUND

Fracking has unlocked an abundance of low cost methane, over 21 trillion proven reserves. This methane will be combusted or converted into hydrogen ($H_2$), which releases greenhouse gas emissions, unless new technologies are developed. In the US, almost all 10 million tons of $H_2$ per annum (Mtpa) results from steam methane reforming (SMR) and produces 100 Mtpa $CO_2$. The energy content of the produced $H_2$ represents approximately 1% of US energy consumption and 2% of domestic $CO_2$ emissions. The $H_2$ market is growing at a compound annual growth (CAGR) of over 6% motivating a shift towards low-carbon production methods such as water electrolysis or carbon capture.

Steam reforming of natural gas is the current state of the art in hydrogen production. As an alternative approach, water electrolysis is energy intensive and dependent upon low electricity prices to maintain price parity with steam reforming. Similarly, carbon capture approaches suffer from the absence of carbon credits and geological restraints for carbon sequestration and storage systems.

Steam reforming of natural gas involves reacting it with steam in the presence of a metal catalytic, such as nickel (Ni), in a catalytic reactor at high temperatures in the range of 700-1100° C., and modest pressure, in the range of 3-25 bar. The overall reaction produces 4 moles of $H_2$ per mole of $CH_4$ but the user of natural gas for process heat reduces the hydrogen yield by 60-75% and is associated with CO2 emissions, in the range of 10 kg $CO_2$ per kg $H_2$. The product gases are cooled and passed onto a pressure swing absorber (PSA) vessel to yield high purity $H_2$, greater than 99.9%. However, the presence of CO contaminant is incompatible for use in electromechanical applications, particular fuel cells, necessitating additional expensive purification steps. Partial oxidation (POX) and coal gasification (CG) are alternative approaches to use fossil fuels for $H_2$ production. The addition of a $CO_2$ capture and sequestration system results in increased $H_2$ production costs being comparable to that of energetically-intensive water electrolysis. Water electrolysis has been touted as a method of producing emission-free $H_2$, but projections continue to put it far out of reach of economic competition with SMR. Table 1 shows a comparison of the embodiments to steam reforming and water electrolysis.

TABLE 1

Comparison of proposed technology with the steam-reforming, water electrolysis using solid oxide electrolyzers and methane pyrolysis.

| Metric | Steam Reforming | Water Electrolysis | Natural Gas Pyrolysis (Molten Metal) |
|---|---|---|---|
| Enthalpy of reaction (kJ/mol $H_2$) | 63 | 143 | 37 |
| Process $CO_2$ Emissions (kg/kg $H_2$) | 7.5 | ~0 | 0-1.1 |
| Operating temperature (° C.) | 700-1100 | 600-800 | 650-1400 |
| Pressure of $CH_4$ (bar) | 3-25 | Ambient | 1-20 |
| Conversion efficiency (%) | 95 | 95 | >90 |
| Capital cost ($/ton per year $H_2$) | >1800 | >2700 | <900 |
| $H_2$ production cost ($/kg $H_2$) | 1.25 | $ 3.16 | 1.25 (no C revenue) |

Methane pyrolysis, $CH_4 \rightarrow C+H_2$, has long promised an energy-efficient approach to emission-free hydrogen production and techno-economic models predict the feasibility of achieving cost-parity with steam reforming through revenue from carbon production. However, achieving cost parity in the absence of carbon revenue is challenging due to the unfavorable stoichiometry compared to steam methane reforming, $CH_4 + 2H_2O \rightarrow CO_2 + 4H_2$. This overall exergy balance results in methane pyrolysis requiring more $CH_4$ feedstock, on the order of 30%, requiring low capital costs to achieve cost parity.

Non-catalytic methane pyrolysis needs to overcome a high activation energy barrier of approximately 400 kJ/mol. The high operating temperatures results in increased reactor fabrication costs. Past efforts at methane pyrolysis using high melting point, solid-phase catalysts such as nickel (Ni), iron (Fe), molybdenum (Mo) or cobalt (Co) have lowered activation energy barriers (<300 kJ per mole hydrocarbon feedstock), but are rapidly deactivated because of carbon buildup, or coking. The use of molten metals could potentially enable carbon separation, but existing methods suffers from poor catalytic activity for methane pyrolysis.

The use of catalytically active molten alloys for methane pyrolysis has been recently reported. However, achieving cost parity is unlikely due to the extremely low gas hourly space velocity (GHSV) and high loss rate of the volatile molten metal. The reactor design approaches currently reported, including bubble column, slug, and capillary reactors all have a continuous gas phase with a size-dependent bubble rise velocity. Since the gas residence time is constrained by the low bubble rise velocity, all of these methods suffer from low throughput on account of slow bubble rise velocity.

Currently, no commercially mature technology exists that can produce emissions-free hydrogen at cost parity with steam reforming.

SUMMARY

According to aspects illustrated here, there is provided a system to decompose a hydrocarbon reactant into a gaseous product and a solid product having a reactor volume containing liquid catalyst, a mechanism to distribute the liquid catalyst into the reactor volume as a liquid mist through a first inlet, a distributor to distribute a hydrocarbon reactant through a second inlet into the reactor volume, a heat source positioned to maintain a temperature between 1100° C. and 1400° C. in the reactor volume, a separator to separate the solid product from the liquid catalyst, a re-circulation path to re-circulate the liquid catalyst back to the reaction chamber, and an outlet to allow at least one output gas to be removed from the reactor volume.

According to aspects illustrate here, there is provided a system to distribute a liquid to an enclosed volume in the form of a mist, comprising a plurality of orifices designed to break up the liquid into a mist, the mist having droplets with a liquid fraction within the enclosed volume greater than five percent.

According to aspects illustrated here, there is provided a method to decompose a hydrocarbon reactant into a gaseous product and a solid product that includes generating a mist of a liquid catalyst within a reactor volume, heating the reactor volume to a temperature between 1100° C. and 1400° C., introducing a hydrocarbon reactant into the reactor volume to produce a solid product and a gaseous product, separating the solid product from the liquid catalyst, removing the solid product and gaseous product from the reactor volume, and recirculating the liquid catalyst be re-introduced to the reactor volume.

DETAILED DESCRIPTION OF THE EMBODIMENTS

The embodiments here involve a liquid mist reactor that decomposes natural gas or any hydrocarbon to produce hydrogen gas and solid carbon, longer chain hydrocarbons (for example: $2CH_4 \rightarrow C_2H_4+2H_2$), shorter chain hydrocarbons (for example: $C_4H_{10} \rightarrow 2CH_4+C_2H_2$) or any combinations of those. The embodiments enables low-cost $H_2$ production through a combination of a catalytically active liquid to improve pyrolysis kinetics and a liquid mist reactor designed to improve catalyst surface area. The catalytic liquid allows for high production flux, and the mist reactor design allows for a high surface area on which the reaction occurs. These use of liquid mist catalysts provides a very high catalyst surface per unit reactor volume, enable extremely high reactor vessel utilization to be achieved ($100-10^7$ $h^{-1}$). The terms mist, aerosol and spray are used interchangeably, and unless specified otherwise, refer to a fine suspension of liquid droplets or solidified particles in a gas. The size of the produced droplets or solids in the mist may vary from 0.1 to 1000 microns in diameter. In case the droplets are non-spherical, the droplet size is defined as the mass-averaged equivalent diameter of the non-spherical droplet.

Figure 1:
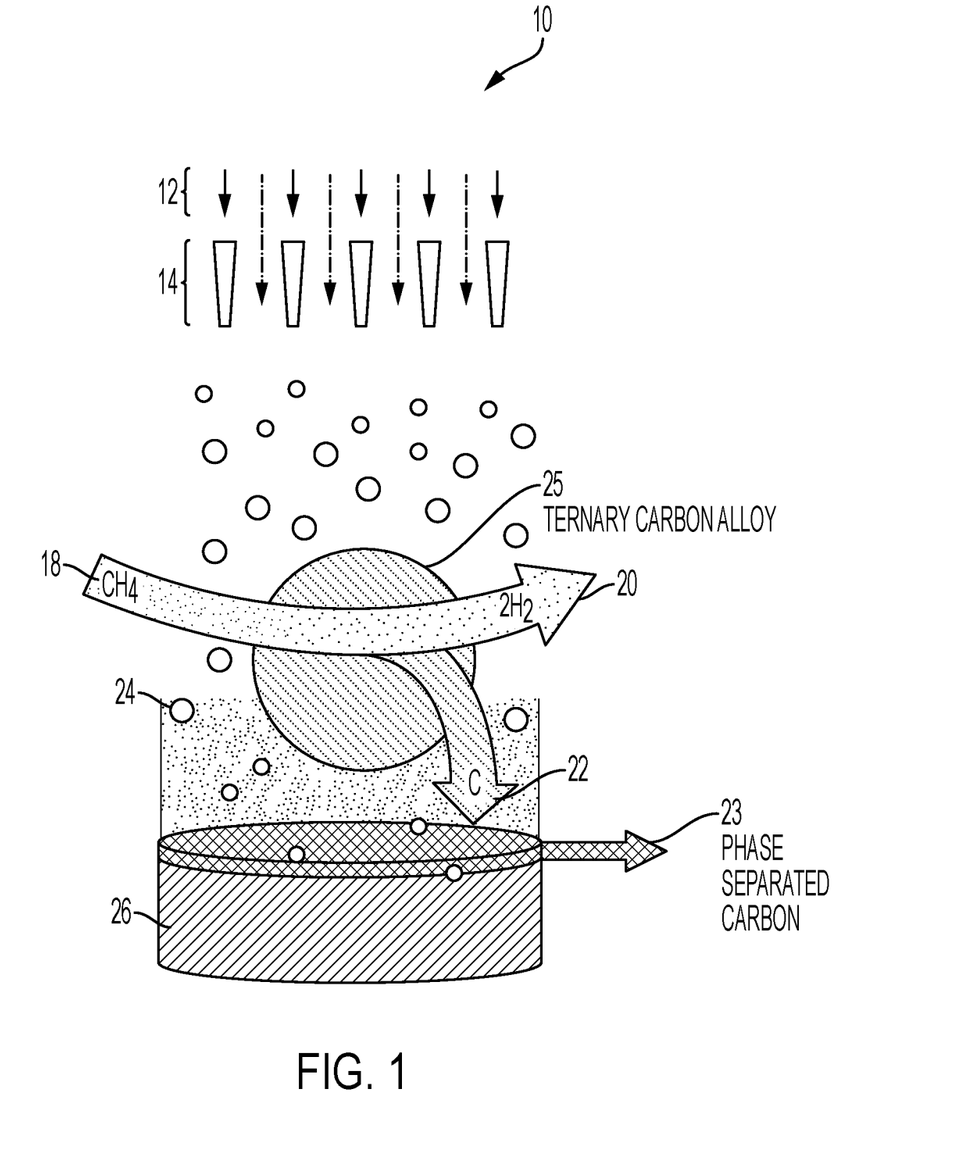
FIG. 1 shows an embodiment of a liquid mist catalyst methane pyrolysis reactor.

FIG. 1 shows a diagram of an approach set forth in the embodiments. The liquid mist reactor 10 has a liquid catalyst 12. As will be discussed in more detail further, the catalyst may reside inside a reservoir inside the reactor, or external to the reactor and later introduced into the reactor. The liquid may be converted into a mist using a set of misting nozzles 14. In various embodiments, either a single nozzle or a plurality of nozzle designs may be used to ensure that the liquid fill fraction within the reactor volume is between 1 percent and 5 percent, or between 5 and 30 percent by volume. The mist of liquid catalyst droplets such as 24 enters the reaction chamber into which is introduced methane ($CH_4$) through an inlet 18 that may have a co-current, countercurrent, cross-current or an arbitrary position relative to the nozzles 14. The entrance of the mist of liquid catalyst could be at the top of the reactor, as shown, from either side, or from the bottom.

As the hydrocarbon interacts with the liquid catalyst, the reaction results in the production of $H_2$ or alkane, alkene or alkyne-based gases 20, solid carbon outputs 22, and a ternary carbon alloy 25. Some of the carbon may be entrained in the hydrogen gas, which may require further process to harvest and some may exit the reactor as phase-separated carbon 23. Similarly, the carbon may mix with the liquid catalyst and may need further separation. The liquid catalyst mist may pool at the bottom of the chamber such as at 26 and can be recycled and reused, possibly after separation from the solid product of the reaction. As used here, the terms "reaction chamber," "reactor" and "vessel" may be used interchangeably to refer to the volume in which the reaction between the gas and the catalyst takes place. Table 2 shows a comparison of embodiments using this approach and the current state of the art.

TABLE 2

Comparison of methane pyrolysis states of the art and the embodiments

| Metric | Bubble Column | Liquid Mist Reactor |
|---|---|---|
| Reactor fill fraction (%) | 25 | 1-5, 5-30 |
| Reactor SA:V ($cm^2$ catalyst/$cm^3$ reactor) | 1.5 | >0.6-18,000 |
| Reaction rate ($\mu mol$ $CH_4/cm^2 \cdot s$) | 0.79 | >2 |
| Operating temperature (° C.) | 1065 | 650-1400 |
| Pressure of $CH_4$ (bar) | 1.6 | 1-20 |
| Conversion efficiency (%) | 95 | 80-99.999 |
| Space velocity (l/h) | <10 | $100-10^7$ |
| $H_2$ production cost ($/kg) | >3.00 | <1.5 |

The use of molten metal in pyrolysis reactor designs are in the early stages of development, and usually take the form of bubble column, capillary, packed bed, and falling film reactors. However, all these designs suffer from low throughput on account of low bubble rise velocity in slug and bubble column reactors, or low surface area to volume ratio in packed bed and fluid wall flow reactors. The differential reactor conversion (dX) can be explained in terms of the design equation to predict the conversion in terms of differential residence time ($d\tau$), reaction flux ($r_{CH4}$) and specific surface area (a):

$$d(X) = r_{CH_4} * a * d\tau.$$

Figure 6:
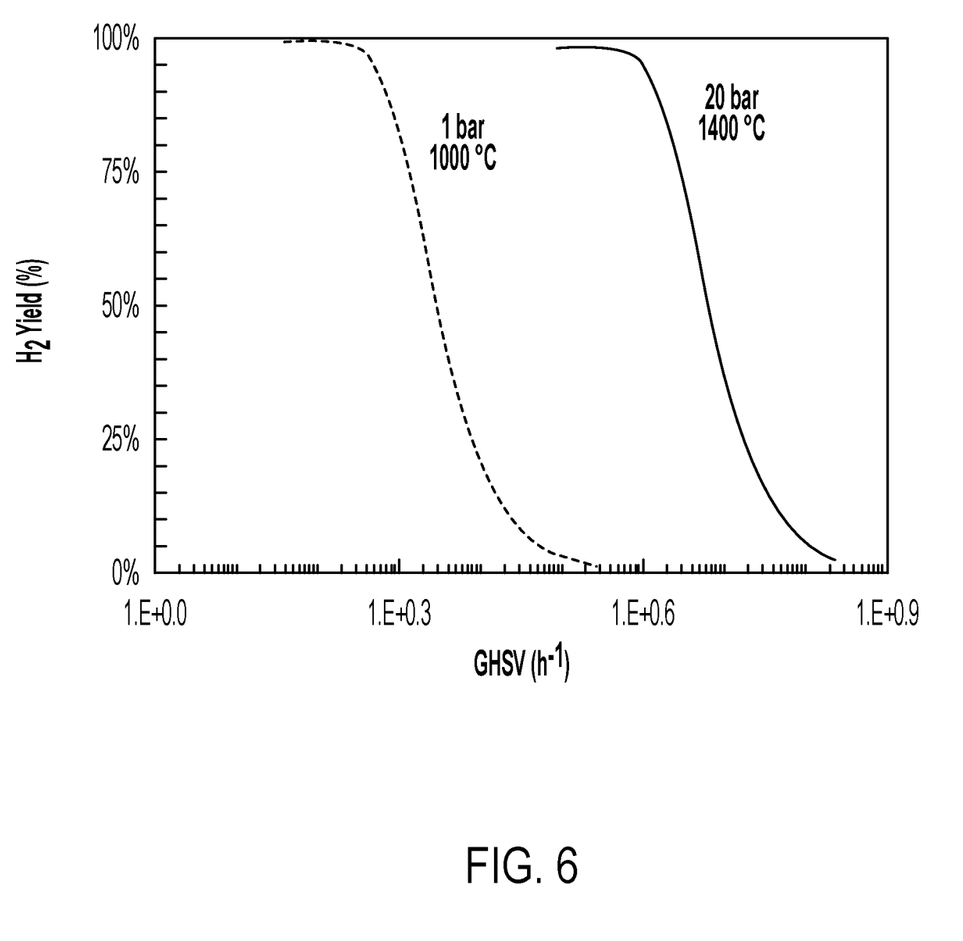
FIG. 6 shows a graph of an expected range of performance for a methane pyrolysis reactor.

In bubble column reactors, the residence time ($\tau \propto \sqrt{D_b}$) and specific surface area $$\left(a \propto \frac{1}{D_b}\right)$$

are simultaneously depending upon bubble size ($D_b$). Achieving high conversion rates necessitates high specific surface area, usually meaning small bubble size. However, small bubble size unfortunately also reduces bubble buoyancy and thereby reactor throughput. To reduce reactor capital costs, the process needs reactor designs that circumvent this constraint. The use of mist reactors along with liquid catalysts at high temperature enables extremely high reactor throughput to be achieved. In practice, the expected throughput, or gas hourly space velocity (GHSV) required for 90 percent hydrogen yield can vary from approximately 100 h$^{-1}$ (1000° C., PCH$_4$=1 bar) to approximately 10$^7$ h$^{-1}$ (20 bar, 1400° C.). The expected range of performance is summarized in FIG. 6. These reactor throughput values are far higher than reportedly achievable using existing reactor designs.

The embodiments here include a reactor design, a liquid catalyst composition of matter and a nozzle design to form a mist of the liquid catalyst. FIGS. 2-5 show alternative embodiments of the reactor design. Components that are similar between the various embodiments will be identified using the same reference numbers.

In general, the system will include a reactor volume containing liquid catalyst, where "containing" includes a pre-loaded catalyst or where the catalyst is added into the vessel from an external source. The system will also include a mechanism to distribute the liquid catalyst, a distributor to distribute a hydrocarbon gas through an inlet into the reactor volume, a heat-transfer source positioned to uniformly distribute the temperature by either adding or removing heat, a separator to separate out the solid pyrolysis from the liquid catalyst and a way to remove the output gas from the volume. The heat sources may exchange heat between streams of the hydrocarbon reactant and the solid pyrolysis product to maintain a process energy efficiency of at least 25 percent. In one embodiment, the reactor may operate at a temperature of less than 1400° C. and pressures of up to 20 bar.

The hydrocarbon gas, also referred to as the hydrocarbon reactant, may comprise at least one selected from the group consisting of: natural gas; liquefied petroleum gas; gasoline; diesel; kerosene; naphtha; JP-8 (a kerosene-based fuel with additives that meets the standards of MIL-DTL-83133); methane; ethane; propane; butane; pentane; hexane; benzene; xylene; toluene; and any combination thereof. Further, the hydrocarbon may also refer to all alkanes, alkenes, alkynes and arenes with a boiling point less than 600° C.

Figure 2:
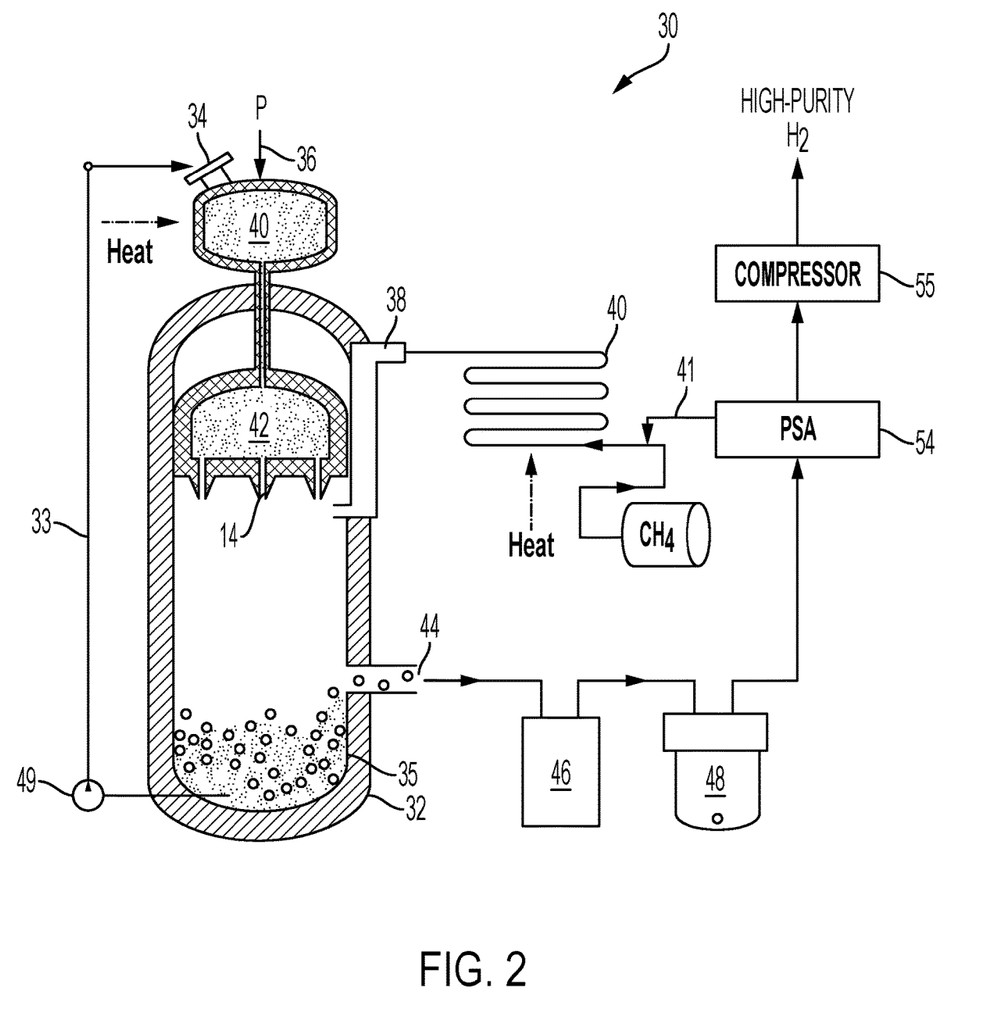
FIG. 2 shows another embodiment of a liquid mist catalyst methane pyrolysis reactor.

In the system 30 of FIG. 2, the reactor vessel 32 has an inlet 34 through which a liquid catalyst loads into the vessel. In this embodiment, a pre-heating chamber 40 heats the catalyst to make it easier to turn it into a mist or it is heated in the internal reservoir 42. For some materials, this may involve melting the material into a liquid catalyst. The liquid catalyst is transferred into the reactor chamber 32 through a series of nozzles or orifices such as 14 that convert the liquid catalyst into a mist. The use of a mist increases the available surface area for reactions, resulting in a higher conversion efficiency. Pressure may be added at 36 to assist with this process. In one embodiment, the average diameter of the particulate in the mist is between 1 and 1000 microns, and the droplet fill fraction is between 1 and 25 percent.

The hydrocarbon gas is also introduced into the chamber 32 through the inlet or port 38. As mentioned before, the hydrocarbon gas inlet may be located at any spot on the vessel. In this particular embodiment, the hydrocarbon gas is methane and is heated by heater 40 prior to entering the chamber and there is a hydrocarbon recirculation channel 41. The reaction in the chamber between the liquid catalyst mist and the hydrocarbon gas results in a separation of hydrogen and carbon from the gas. Some of the carbon, which will typically comprise a solid, will fall to the bottom of the chamber, mixed in with the unreacted liquid catalyst.

The chamber 32 may have a liner 35, such as a ceramic or other type of liner, which is a barrier between the liquid catalyst and material of construction of reaction vessel 32. The catalyst is subsequently recovered through recirculation line 33, which also includes the use of an appropriate high-temperature pump 49 to recirculate the liquid catalyst.

Some of the carbon may also be entrained in the hydrogen gas that exits the chamber through the outlet 44. This may be captured using a filter, such as a knock out pot 46, and a second filter 48. These allow extraction of the solid carbon from the hydrogen gas. In this particular embodiment, the gas may go through a pressure swing adsorber (PSA) 54 and a compressor 55 to output high-purity product gas. In one embodiment, the output hydrogen may be 99.999% pure at 10 bar of pressure.

Figure 3:
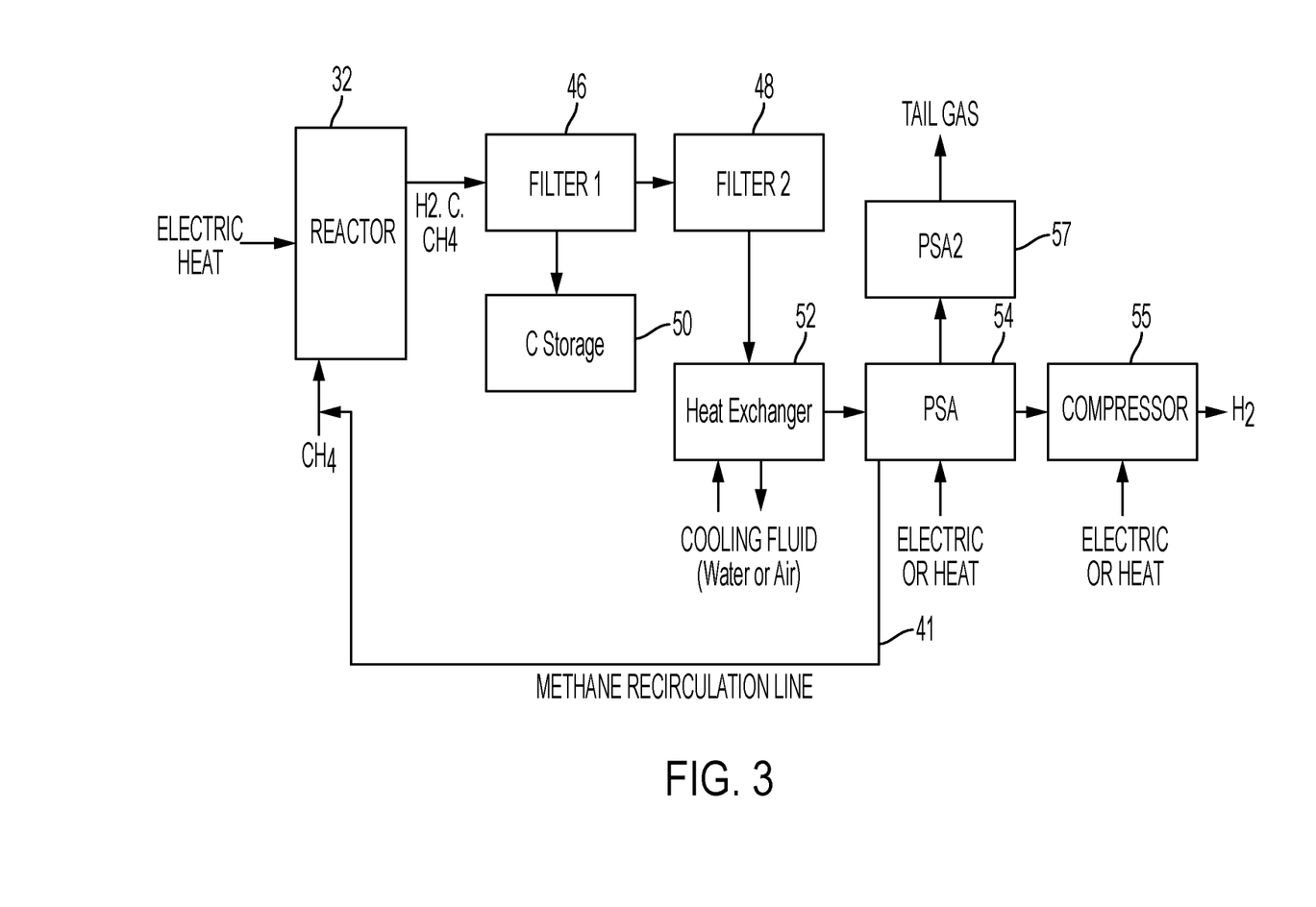
FIG. 3 shows an embodiment of a piping diagram for a liquid mist catalysis methane pyrolysis reactor.

FIG. 3 shows a piping diagram for an embodiment making a bubble column reactor 32. The reactor 32 receives the electric heat and the methane or other hydrocarbon gas. Typically, the liquid catalyst will enter the chamber from the top of the reactor. The outlet transfers the hydrogen with entrained carbon and any unreacted hydrocarbon gas to a first filter. For example, the first filter 46 may comprise a cyclone filter or a knock-out pot. The cyclone filter 46 may be attached to a carbon storage 50. After going through the cyclone filter, a further filter 48, such as a cartridge filter, may catch any remaining solid carbon. The hydrogen may then be cooled at 52 and sent to a to an optional pressure swing adsorber (PSA) bed 54 for purification to yield up to 99.999% pure H$_2$. The unconverted methane is recirculated to the reactor feed stream, and residual tail gas composed of H$_2$, natural gas and inerts may pass through a second PSA 57 may be used for process heating value. The H$_2$ may optionally be compressed using a compressor 55 and then output.

Figure 4:
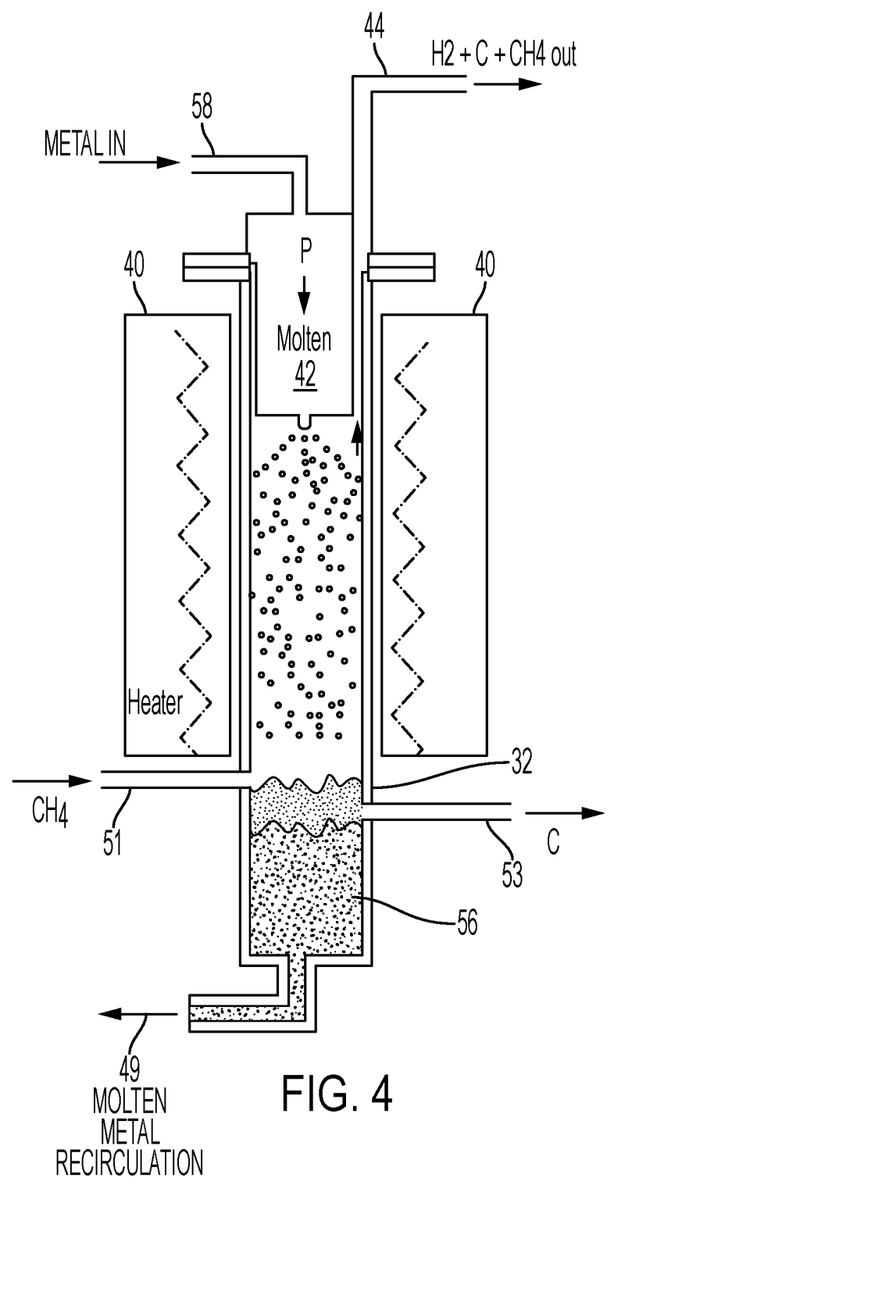
FIG. 4 shows an embodiment of a liquid mist catalyst methane pyrolysis reactor.

FIG. 4 shows an alternative embodiment of a reactor. In this embodiment the liquid catalyst may already reside inside the reactor vessel in the reservoir 32. In addition to the nozzle 14, the liquid catalyst is continuously recirculated through inlet 58 and converted into a mist within the chamber 32. Additional pressure may be added through the use of a diaphragm located outside the heated zone, such that the gas is not in contact with the liquid catalyst. External heaters 40 operate to keep the reactor vessel at a uniform temperature, typically between 600° C. and 1100° C., or between 1100° C. and 1400° C. The methane or other hydrocarbon gas enters the chamber through the second inlet 51 and upon generation of the output gas, which may include entrained solid carbon, some of the carbon exits the system through the outlet 44. The output product may include unreacted methane, which is captured in the PSA bed and recirculated through inlet 51.

In one embodiment, the liquid catalyst and hydrocarbon inlets and ports may be positioned to achieve a co-current flow in which the liquid catalyst and hydrocarbon flow in the same direction, counter-current flow in which they flow in opposite directions, or cross-current flow, in which they flow orthogonal to each other, within the reactor volume. These reactor configurations are intended to achieve uniform heat transfer; higher conversion; higher reactant throughput; improved carbon-liquid separation or improved carbon-gas separation within the reactor volume. In the same embodiment, the position of liquid catalyst and gas inlet ports may be located at the top, bottom or side of the reactor. The liquid catalyst and reactant may be injected through the same port in at least one embodiment.

In one embodiment, the reactor may be constructed of stainless steel and high nickel and stainless steel alloys. In one embodiment, the reactor may have a liner of quartz and alumina that will allow recapture and recycling of the liquid catalyst. The selection of the liner material may be made dependent upon the material used in the liquid catalyst.

In one embodiment, the reactor may have a top and a bottom, with the top arranged and configured to allow a batch-type atomized or misting spray of the liquid catalyst down into the reactor volume from above. In one embodiment, the reactor vessel will be pre-charged with the liquid catalyst before operation, and brought up to melt/liquid temperatures with reactor wall heaters, such as those shown in FIG. 4.

In one embodiment, the reactor may include augers, rotary or gravimetric separators to remove the carbon product layer that gravimetrically settles on top of the pool of liquid catalyst 56. The carbon would be removed through outlet 53 and the system include high temperature ceramic gear pumps or electromagnetic pumps to recirculate liquid catalyst at 49. The temperature of operation of molten metals is intended to be maintained between 650° C. and 1400° C.

Figure 5:
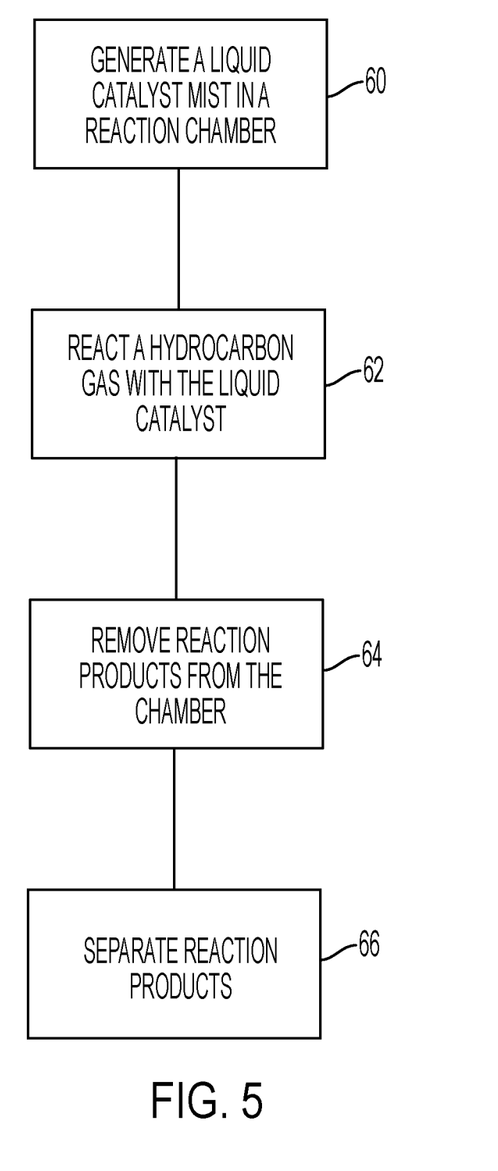
FIG. 5 shows a flowchart of an embodiment of a method to perform methane pyrolysis.

FIG. 5 shows a flowchart of an embodiment of a method of performing hydrocarbon pyrolysis. At 60, the process generates a mist of liquid catalyst into a reaction chamber, which may occur before or during the introduction of the hydrocarbon gas. At 62 the hydrocarbon gas reacts in the chamber with the liquid catalyst. The process 64 removes the reaction products from the chamber, wherein the reaction products will include at least hydrogen gas and solid carbon, as well as the possibility of other byproducts. For example, if a gas is used to atomize the catalyst, it may also become one of the products that exits the chamber. The separation of the reaction products 66 may occur from within the vessel, such as by harvesting the solid carbon from the bottom of the vessel, or after the products exit the vessel. The gaseous product removed from the system may include at least one of hydrogen, ethane, ethylene, acetylene, propylene, benzene or any combination of those. The liquid catalyst may also be separated from the solid product to allow it to be re-used. This increases catalyst longevity and may reduce operating costs.

The system may operate such that a difference between enthalpy of the hydrocarbon reactant and solid pyrolysis product is no higher than enthalpy of fusion of the liquid catalyst contained within the reactor volume. This is achieved by ensuring that the enthalpy of reaction within the reactor volume is at least higher than the enthalpy of fusion of the molten alloy. This maintains the gas temperature in case of an endothermic reaction such as methane pyrolysis. Mathematically, this is stated as below:

$$\Delta H_R < \Delta H_{fusion}$$

In experiments, a TGA furnace was used as a model reactor. Diluted methane at 5% volume was flowed past a single $Ni_{0.2}Ga_{0.8}$ catalyst bead (251 mg) and pyrolyzed at 850° C. and near-complete initial conversion was achieved at 95%. The high conversion efficiency and comparable GHSV are particularly remarkable since the SA:V ratio and operating conditions used in this un-optimized setup could easily be improved to meet our higher GHSV milestone.

The carbon produced in the TGA experiments was characterized using scanning electron microscopy and energy dispersive spectroscopy (EDS). The results suggest that physical morphology of the carbon phase is highly depending upon the catalyst used and varies from fibers (Ga and Ni—Ga), graphitic (Cu), and aggregated (Ni). This dependency encourages the possibility for control over the control properties and the ability to tailor the properties for use in various applications. Carbon fibers with aspect ratio up to 150:1 and up to 250 micrometers length were observed, and contained up to 12 weight % metal. SEM micrographs support the feasibility of complete de-wetting and separation of metal and carbon phases.

As mentioned previously, in addition to the reactor design, the embodiments may include a misting nozzle that facilitates the break-up of the liquid catalyst. In one embodiment, the liquid catalyst droplet size ranged from 150-500 micrometers, or microns. In one embodiment, the nozzles have a diameter of 250 micrometers. In one embodiment, the misting nozzle comprises an array of misting nozzles that generate a mist that has a surface area to volume ratio greater than 1 $cm^2$ per 1 $cm^3$ of reactor volume. A device may be attached to the plurality of orifices to increase the hydrostatic pressure of the liquid upstream of the plurality of orifice ejectors. In one embodiment, the device operates at a pressure head of less than 10 bar. In one embodiment the size of liquid droplets produced by the nozzles has a mass-averaged diameter of less than 10 micrometers. Additional nozzle modifications are included embodiments that would allow controlled production of liquid droplets with a mass-averaged diameter between 0.1 micrometers and 1000 micrometers.

An experiment was conducted using such a nozzle to spray molten gallium (Ga) into droplets using a misting nozzle. The experiment resulted in 150-500 micrometer diameters droplets under an applied pressure of 3 bar.

Using fill fraction modeling correlations were developed for the breakup of viscous liquid jets to develop relationships between the characteristic nozzle pitch, median drop size, and break-up length. The median jet width ($D_0$), drop diameter ($D_p$), drop breakup length (L) can be estimated from the equations below:

$$D_0 = \Delta P / \gamma;$$

$$Dp \approx 2.1\ D_0$$

$$L = 4.903\mu\sqrt{\frac{D_0}{\rho\gamma}} + 4.559\ D_0.$$

These calculations suggest that stable fill fraction of 15.4% can be expected if a nozzle pitch comparable to the drop diameter (1.25 $D_p$) and drop spacing is comparable to the jet breakup that occurs at length. Using helical grooves in misting nozzles creates a rotating jet and corresponds to a fill fraction of 25%.

In one embodiment, the array of orifices has a pitch of greater than 1.25 times a diameter of the orifice opening. In one embodiment the In addition to the nozzle design, the composition of a novel liquid catalyst to facilitate the catalysis of the hydrocarbon gas. In one embodiment, the liquid catalyst here comprises a composition of matter having a melting point of less than 1100 degrees Celsius, and an activation energy of less than 300 kJ per mol for hydrocarbon pyrolysis. In another embodiment, the composition of matter has the above two characteristics and also has a carbon solubility of at least 1 atomic percent.

In one embodiment, the liquid catalyst may comprises a multi-component alloy made up of at least two different components, one with a relatively low melting point, and the other that is catalytically active. In another embodiment, one catalyst may have both of those properties, such as a eutectic material. In another embodiment, there may be a second or third component that has carbon solubility of at least 1 atomic percent.

In one embodiment, the liquid catalyst includes at least one of the group consisting of lithium; sodium; calcium; potassium; cadmium; aluminum; antimony; bismuth; cerium; copper gallium; indium; lanthanum; lead; magnesium; mercury; silver; tin; and zinc. The total atomic percent composition of the abovementioned elements in the catalyst phase is at least 50 percent and at most 90 percent.

In one embodiment, the liquid catalyst includes at least one of the group consisting of: nickel; iron; cobalt; and manganese. The total atomic percent composition of the abovementioned elements in the liquid catalyst phase is at least ten percent and at most 50 percent In one embodiment, the liquid catalyst includes at least one of the group consisting of chromium scandium; titanium; vanadium; molybdenum; silicon; tantalum; technetium; tungsten; ruthenium; and palladium.

In one embodiment, the liquid catalyst is comprised of a first element having a concentration of at least 0 but not more than 90 weight percent, the first element selected from the group consisting of lithium; sodium; calcium; potassium; cadmium; aluminum; antimony; bismuth; cerium; copper gallium; indium; lanthanum; lead; magnesium; mercury; silver; tin zinc. The liquid catalyst is comprised of a second element having a concentration of at least 11 but not more than 90 weight percent, the second element selected from the group consisting of nickel; iron; cobalt; manganese; chromium; scandium; titanium; vanadium; molybdenum; silicon; tantalum; technetium; tungsten; ruthenium; and palladium.

The system may include a liquid catalyst reservoir integrated with the heat-transfer source to maintain a reservoir temperature of up to 1400° C. In one embodiment the reservoir temperature may be at the melting point of the catalyst of 900° C., 1000° C., or 1100° C. In another embodiment the reservoir may have a temperature of at least 500° C.

In experiments, the liquid catalyst was loaded into a reactor and heated to a desired temperature under a controlled methane partial pressure. Carbon deposition was recorded as a mass gain, and the product gas was fed was fed to a gas analyzer to detect impurities and to serve as a confirmatory measure of $H_2$ production. Control experiments were performed on a gallium sample in an argon atmosphere and demonstrated negligible weight gain. This indicates the possibility of sample oxidation. The pyrolysis rate was measured across a wide temperature range (600-950° C.) using a thermogravimetric analyzer (TGA) coupled and limited feed partial pressure ($P_{CH4}$<0.1 bar). The control experiment performed using methane (0.05 bar $CH_4$) at 800° C. demonstrated that less than 5% could be attributed to non-catalytic methane pyrolysis. The demonstrated $H_2$ production fluxes (summarized in Table 3) are in agreement with existing reports of methane pyrolysis catalysts.

TABLE 3

Comparison of $H_2$ flux using molten catalysts at 800° C. and $P_{CH4}$ = 0.05 bar.

| Catalyst | $H_2$ Flux (mol cm$^{-2}$ s$^{-1}$) |
|---|---|
| $Ni_{0.2}Ga_{0.8}$ | $2.24 \times 10^{-7}$ |
| $Ni_{0.2}Sn_{0.8}$ | $1.60 \times 10^{-7}$ |
| $Ni_{0.2}Bi_{0.8}$ | $1.47 \times 10^{-7}$ |

The expected activation energy for methane pyrolysis using these catalyst materials is expected to be between 50 and 300 kJ/mol. The choice of liquid catalyst materials includes molten pure elements, binary alloys, ternary alloys, quaternary alloys other multicomponent (>4 elements) alloys.

One of the criteria for selection of liquid catalyst materials also includes the use of materials with high solubility for carbon produced through pyrolysis. In this case, the produced carbon is intended to form a liquid solution in the molten phase to enable ease of carbon separation. The dissolution of carbon enables its removal as a homogenous liquid, and the carbon is subsequently phase-separated and removed from the liquid catalyst. The carbon solubility is expected to range from 1 to 25 atomic percent carbon, and is comprised of the one or more of the materials listed in Table 4. However, this is not an exhaustive list—the choice of liquid catalyst materials is also expected to include molten salts such as alkali metal acetylides.

TABLE 4

Comparison of carbon solubility in liquid metal phase at the eutectic point.

| Low solubility | | Intermediate solubility | | High solubility | |
|---|---|---|---|---|---|
| Element | C content (atomic %) | Element | C content (atomic %) | Element | C content (atomic %) |
| Zn | 1.00 | Ni | 6.93 | Rh | 15.5 |
| Sc | 1.11 | Hf | 6.95 | Pt | 16.5 |
| Si | 1.16 | Y | 6.96 | Fe | 16.9 |
| Li | 1.17 | Nb | 10.5 | Mo, Re | 17.0 |
| B | 1.35 | Ce, Pr | 10.6 | Os | 17.5 |
| U | 1.95 | Mn | 11.1 | Tc | 20.2 |
| Ti | 1.96 | Co | 11.9 | Pd | 20.3 |
| Zr | 2.96 | Th | 12.0 | La | 20.6 |
| Cu | 4.00 | Ru | 13.4 | Ir | 20.7 |
| Au | 4.70 | Cr | 13.9 | W | 22.9 |
| | | V | 15.0 | Ta | 23.5 |

Removal of the solid pyrolysis product, typically a carbon-based substance, may involve a multiphase separation unit having at least one of a particulate filter, an electrostatic precipitator, a cyclone filter, a knock-out pot, or a cartridge filter. The carbon product produced may include at least one of: carbon black, carbon fiber, carbon nanofiber, carbon nanotubes, carbon nanocage, fullerene, graphite, amorphous carbon, needle coke, coke or diamond. The selection of the liquid catalyst may affect which carbon product is produced.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed is:

1. An apparatus to decompose a hydrocarbon reactant into a gaseous product and a solid product comprising:
   a reactor volume,
   a reservoir of liquid material;
   a plurality of connected to the reservoir of liquid material, the plurality of nozzles configured to distribute the liquid material into the reactor volume from the reservoir as a liquid mist;
   a gas inlet connected to a hydrocarbon gas source to receive hydrocarbon gas reactant;

a distributor connected to the inlet to distribute the hydrocarbon gas reactant into the reactor volume;

a heat source located adjacent the reactor volume configured to generate sufficient heat in the reactor volume to maintain a temperature between 1100° C. and 1400° C. in the reactor volume;

a separator to separate the solid product from the liquid material;

a re-circulation path connected between the reactor volume and the reservoir to re-circulate the liquid material from the reactor volume to the reservoir;

a gas outlet connected to the reactor volume configured to outlet hydrogen gas from the reactor volume; and at least one filter connected to the gas outlet to remove entrained solid product from the hydrogen gas.

2. The apparatus as claimed in claim 1, wherein the liquid material has a melting point between −40° C. and 1400° C. and comprises:

a first element of a concentration of up to 90 weight percent, the first element selected from the group consisting of lithium; sodium; calcium; potassium; cadmium; aluminum;

antimony; bismuth; cerium; copper, gallium; indium; lanthanum; lead; magnesium; mercury;

silver; tin and zinc; and a second element of a concentration of at least 11 weight percent, the second element selected from the group consisting of nickel; iron; cobalt; manganese; chromium scandium;

titanium; vanadium; molybdenum; silicon; tantalum; technetium; tungsten; ruthenium; and palladium.

3. The apparatus as claimed in claim 1, wherein the liquid material comprises one or more components:

wherein the one or more component has an activation energy barrier for hydrocarbon pyrolysis of less than 300 kJ per mole; or wherein the one or more component has a carbon solubility of at least 1 atomic percent.

4. The apparatus as claimed in claim 1, wherein the liquid material reservoir is positioned adjacent the heat source.

5. The apparatus as claimed in claim 1, wherein the plurality of nozzles to distribute the liquid material comprises one of either:

a plurality of nozzles configured to produce the mist of liquid material into the reactor volume through the breakup of a liquid jet wherein the mist has a surface area to volume ratio greater than 1 cm$^2$ per 1 cm$^3$ of reactor volume; or a plurality of nozzles configured to produce the mist as liquid droplets having a size of a mass-averaged diameter between 0.1 and 1,000 microns.

6. The apparatus as claimed in claim 1, where the nozzles comprises one of:

a plurality of misting nozzles to produce a mist of liquid material in the reactor volume through breakup of a liquid jet; or a plurality of misting nozzles to accelerate the breakup of a liquid jet through patterned grooves within the misting nozzles.

7. The apparatus as claimed in claim 1, wherein the reactor volume is configured to process one of co-current, counter-current, or cross-current flows of hydrocarbon reactant and liquid material mist.

8. The apparatus as claimed in claim 1, wherein the liquid material is introduced into the reactor volume through an outlet at the top, side, or bottom of the reactor volume.

9. The apparatus as claimed in claim 1, wherein the hydrocarbon reactant comprises at least one selected from group consisting of: natural gas;

liquefied petroleum gas; gasoline; diesel; kerosene; naphtha; kerosene-based fuel; methane;

ethane; propane; butane; pentane; hexane; benzene; xylene; toluene; and any combination thereof; alkynes; alkenes; alkanes; arenes; cyclic compounds and any combination thereof having a boiling point less than 600° C.

* * * * *